(12) United States Patent
Lai et al.

(10) Patent No.: US 7,800,759 B2
(45) Date of Patent: Sep. 21, 2010

(54) EYE LENGTH MEASUREMENT APPARATUS

(75) Inventors: Ming Lai, Webster, NY (US); Daozhi Wang, Rochester, NY (US); Barry T. Eagan, Spencerport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 103 days.

(21) Appl. No.: 11/954,146

(22) Filed: Dec. 11, 2007

(65) Prior Publication Data

US 2009/0147266 A1   Jun. 11, 2009

(51) Int. Cl.
*G01B 11/02* (2006.01)
(52) U.S. Cl. ..................................... 356/497
(58) Field of Classification Search ................ 356/479, 356/497; 351/200, 205, 211, 212
See application file for complete search history.

(56) References Cited

U.S. PATENT DOCUMENTS

| | | | |
|---|---|---|---|
| 5,347,327 A | 9/1994 | Sekine et al. | |
| 5,673,096 A | 9/1997 | Dorsel et al. | |
| 5,975,699 A | 11/1999 | Hellmuth | |
| 6,053,613 A * | 4/2000 | Wei et al. | 351/205 |
| 6,144,456 A | 11/2000 | Chavanne et al. | |
| 6,243,191 B1 | 6/2001 | Fercher | |
| 6,779,891 B1 | 8/2004 | Barth et al. | |
| 7,246,905 B2 | 7/2007 | Benedikt et al. | |
| 7,370,968 B2 * | 5/2008 | Hanebuchi | 351/211 |
| 7,400,410 B2 * | 7/2008 | Baker et al. | 356/498 |
| 2005/0140981 A1 | 6/2005 | Waelti | |
| 2006/0146334 A1 | 7/2006 | Cluff et al. | |
| 2007/0076217 A1 | 4/2007 | Baker | |
| 2007/0291276 A1 * | 12/2007 | Fercher | 356/497 |
| 2008/0285043 A1 | 11/2008 | Zeiss | |

FOREIGN PATENT DOCUMENTS

| | | |
|---|---|---|
| EP | 1 582 143 A | 10/2005 |
| WO | WO 2006/081998 A1 | 8/2006 |
| WO | WO 2007/065670 A | 6/2007 |

OTHER PUBLICATIONS

Ballif et al., "Rapid and scalable scans at 21 m/s in optical low-coherence reflectometry," Optics Letters, (vol. 22), (Issue. 11), (p. 757-759), (Jun. 1, 1997).
International Search Report (PCS/ISA/210) and Written Opinion (PCT/ISA/237) mailed on Sep. 2, 2009.

* cited by examiner

*Primary Examiner*—Michael A Lyons
(74) *Attorney, Agent, or Firm*—Jeffrey B. Powers (57) ABSTRACT

An interferometric axial eye length measurement apparatus having a light source adapted to produce a beam of partially coherent light, a first mirror and a second mirror disposed in the reference arm, and a processor adapted to control at least the second mirror such that a corneal interference peak and a second interference peak have a non-zero separation. There is at least one variable delay optical element having a delay signal, wherein the delay signal corresponding to a region between the corneal interference peak and second interference peak is substantially linear.

19 Claims, 5 Drawing Sheets

EYE LENGTH MEASUREMENT APPARATUS

FIELD OF INVENTION

The present invention relates to methods and apparatus for eye length measurement, and more particularly to methods and apparatus for eye length apparatus using partially coherent light.

BACKGROUND OF THE INVENTION

Axial eye length measurements based on Michaelson interferometer arrangements are known. Generally, such apparatus include a beam splitter that 1) projects partially coherent light into a test arm onto a subject's eye, and 2) projects partially coherent light into a reference arm onto a moveable mirror. By moving the mirror a known amount and measuring an output including combined light reflected from the eye and from the mirror, portions of the output that are influenced by interference of light reflected from the eye and light from the mirror can be identified, and various eye lengths can be measured.

Figure 1:
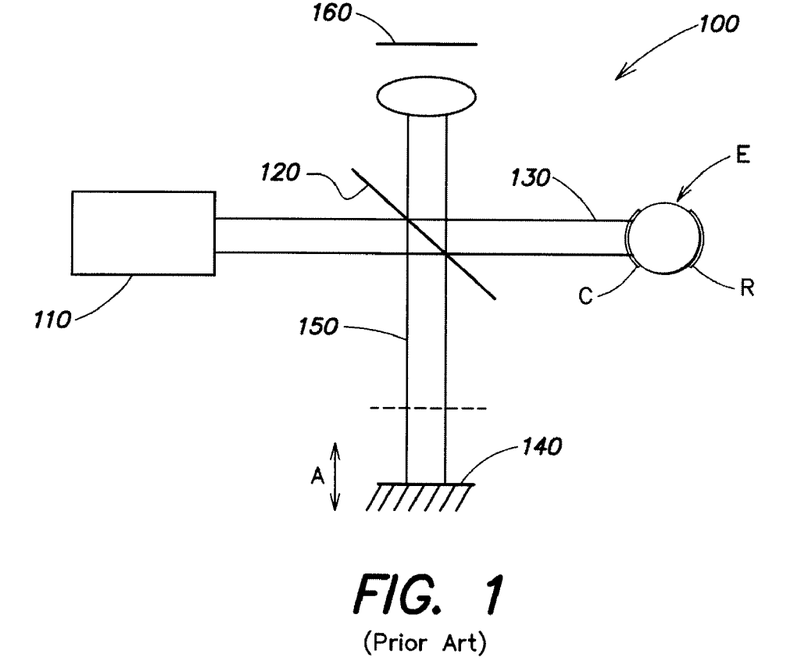
FIG. 1 illustrates a conventional eye length measurement apparatus in which light from a source is projected onto a beam splitter which projects light onto an eye in a test arm and onto a scanning mirror in the reference arm.

Numerous apparatus have been designed to implement such eye length measurement techniques. FIG. 1 illustrates apparatus 100 in which light from a source 110 is projected onto a beam splitter 120 which projects light onto an eye E in a test arm 130 and onto a scanning mirror 140 in a reference arm 150. An output signal from a detector 160 is generated by the combined reflections from the eye and mirror. The amplitude of the signal will increase and decrease due to interference (i.e., interference spikes will arise) when the length of the reference arm is within a distance equal to the coherence length of the light (as determined by the source) of a length in the test arm. A length of the test arm is determined by a reflective surface in the eye (e.g., a surface of the cornea or a surface of the retina). The amount which the mirror is moved between a location to achieve an interference output for a first surface (e.g., a surface of the cornea) and a location to achieve an interference output for a second surface (e.g., a surface of the retina) indicates the distance between the first surface and the second surface. An eye's overall axial length can be measured in this manner.

In apparatus as illustrated in FIG. 1, it is desirable that mirror 140 be moved in a highly linear manner over a substantial length (e.g., 15-35 mm) to obtain accurate eye length measurements. Also, the time required to move the mirror can be substantial, particularly if multiple measurements of a given patient's eye length are to be made and averaged together. As a result, eye movement during measurement can be a source of error.

Figure 2:
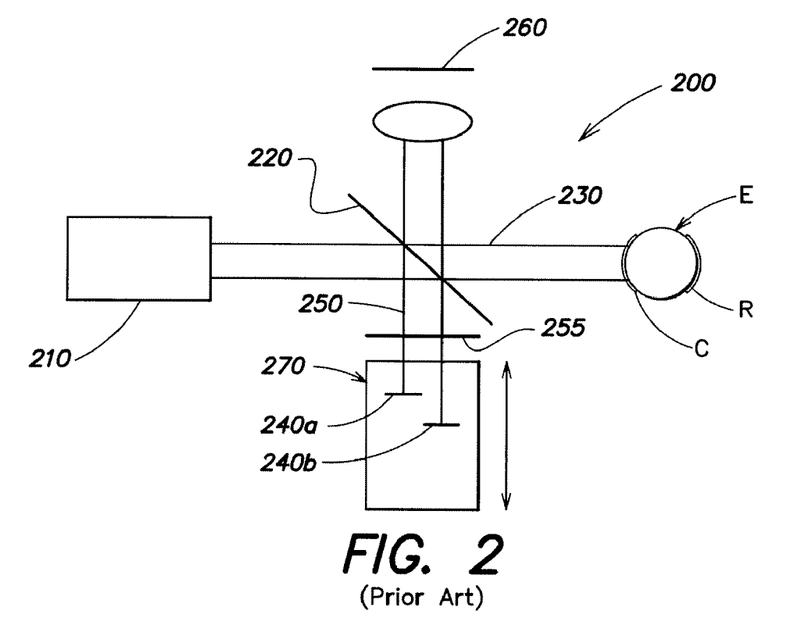
FIG. 2 illustrates another conventional eye length measurement apparatus in which light from a source is projected onto a beam splitter which projects light onto an eye in a test arm and into a reference arm.

FIG. 2 illustrates another eye length measurement apparatus 200 in which light from a source 210 is projected onto a beam splitter 220 which projects light onto an eye E in a test arm 230 and into a reference arm 250. However, in contrast to the apparatus of FIG. 1, the reference arm includes two movable mirrors 240a and 240b. A rotating diaphragm 255 in the reference arm is designed to alternately pass light to the first mirror 240a and second mirror 240b. An output signal from a detector 260 is proportional to a light input signal generated by the reflections from the eye and one of the mirrors. The mirrors are provided in a housing 270 that is scanned back and forth (as indicated by an arrow A) toward and away from beam splitter 220. The amplitude of the signal will increase and decrease due to interference when the length of either or both portions of the reference arm is equal to a length in the test arm that corresponds to a reflective surface of the eye.

SUMMARY

Aspects of the present invention are directed to improving measurement accuracy of interferometric axial eye length measurement apparatus.

An aspect of the invention is directed to an axial eye length measurement apparatus for measuring an eye having a cornea and a second surface. The apparatus comprises a light source adapted to produce a beam of partially coherent light, and a beam splitter disposed in the beam and adapted to project some of the light into a test arm and some of the light into a reference arm. The apparatus also comprises a first mirror disposed in the reference arm to form a first reference path and adapted to intercept a first portion of the light in the reference arm, and a second movable mirror disposed in the reference arm to form a second reference path and adapted to intercept a second portion of the light in the reference arm. The apparatus also comprises a processor adapted to control at least the second movable mirror such that a corneal interference peak formed using the first portion and the light in the test arm and a second interference peak formed using the second portion and the light in the test arm have a non-zero separation. In some embodiments, the separation is predetermined.

In some embodiments, the processor is adapted to control at least the second mirror such that an envelope corresponding to the corneal peak and an envelope of the second peak are separated from one another.

In some embodiments, the apparatus further comprises at least one variable delay optical element extending across the first portion and the second portion, the delay element having a delay signal, wherein the delay signal corresponding to region between the corneal interference peak and second interference peak is substantially linear. In some embodiments, the derivative of the delay signal corresponding to the region between the corneal interference peak and the second interference peak changes by less than 30%.

The apparatus may further comprise a detector arranged to detect the corneal interference peak and the second interference peak, and generate an electric signal output. The apparatus may further comprise a display connected to the detector configured to display the corneal interference peak and the second interference peak. In some embodiments, the processor is adapted to control the first mirror and the second mirror.

Another aspect of the invention is directed to an axial eye length measurement apparatus, comprising an light source adapted to produce a beam of partially coherent light, a beam splitter disposed in the beam and adapted to project light into a test arm and to project light into a reference arm, a first mirror disposed in the reference arm and adapted to intercept a first portion of the light in the reference arm, a second movable mirror disposed in the reference arm and adapted to intercept a second portion of the light in the reference arm, and a variable delay optical element extending across the first portion and the second portion.

Yet another aspect of the invention is directed to a method of measuring an eye length, comprising projecting partially coherent light, directing a first portion of the light onto an eye having a cornea, directing a second portion of the light into a reference arm, a first part of the second portion of the light incident on a first mirror, and a second part of the second portion of the light incident on a second mirror, variably delaying the first part, variably delaying the second part, interfering the first part with the first portion to form a corneal interference peak, interfering the second part with the first portion to form a second interference peak, and positioning the second mirror and the first mirror relative to one another such that the corneal interference peak and second interference peak have a non-zero separation. In some embodiments, the separation is predetermined.

In some embodiments, the steps of variably delaying the first part and variably delaying the second part are achieved using a same variable delay element.

In some embodiments, the predetermined non-zero separation corresponds to a linear portion of a delay signal of an apparatus causing the variable delay. In some embodiments, the delay signal has a derivative that changes by less than 30% between the corneal interference peak and the second interference peak. In some embodiments, the method further comprises displaying the corneal interference peak and the second interference peak.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 3:
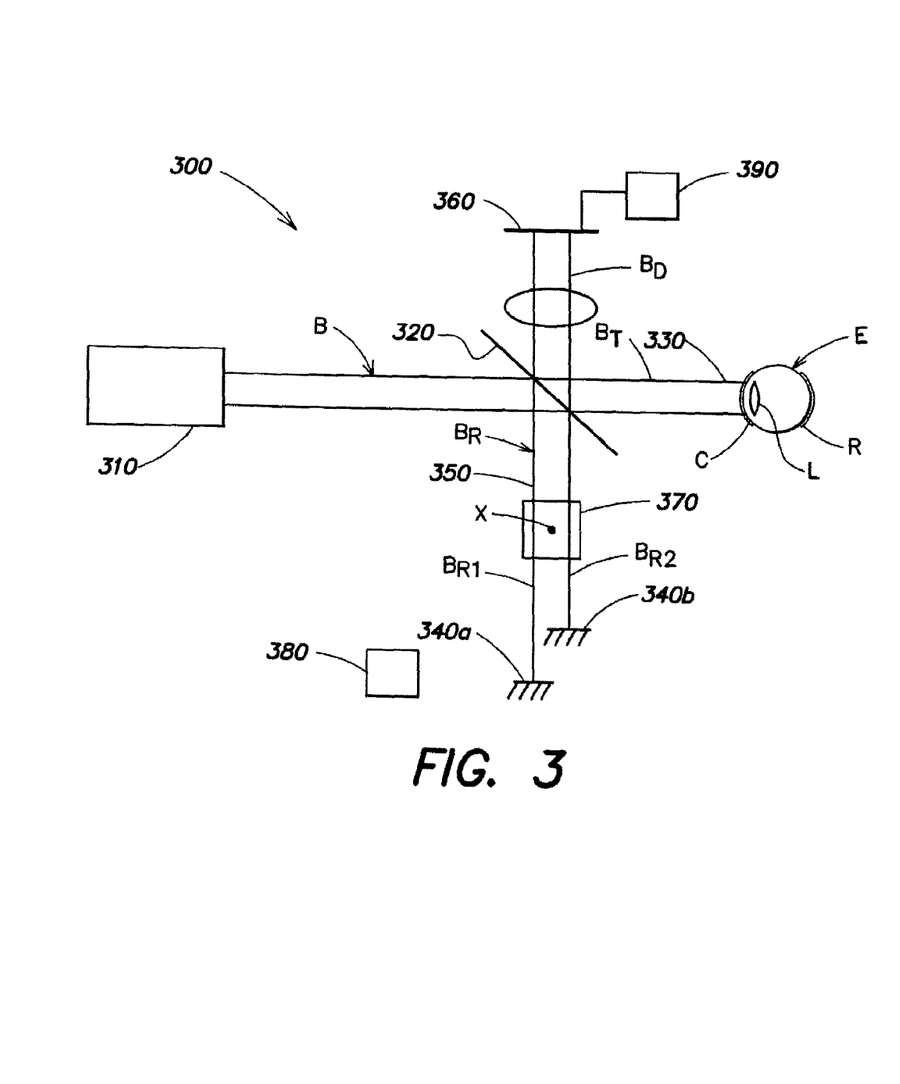
FIG. 3 illustrates an axial eye length measurement apparatus according to aspects of the present invention.

FIG. 3 illustrates an example of an axial eye length measurement apparatus 300 according to aspects of the present invention. Apparatus 300 comprises a light source 310, a beam splitter 320, a first mirror 340a, a second mirror 340b, a variable delay optical element 370 and a detector 360.

Light source 310 is adapted to produce beam B which is formed of partially coherent light. For example, the coherence length of the light source is less than about 10 microns. It will be appreciated that the coherence length may impact the precision with which the reference arm must be located to achieve interference of light reflected back from the test arm and light reflected back from the reference arm, and thereby impact the precision with which length measurements may be made. For example, the light source may be a superluminescent diode.

In any suitable conventional manner, beam splitter 320 is disposed in beam B to project a test beam of light $B_T$ into a test arm 330 and a reference beam of light $B_R$ into a reference arm 350. Light in the test arm is projected onto a subject's eye E, having a cornea C, a retina R, and a lens L.

First mirror 340a is disposed in the reference arm and adapted to intercept a first portion $B_{R1}$ of the reference beam $B_R$. The first mirror is arranged to reflect light in the first portion of the reference beam back onto and through beam splitter 320. The first mirror is also arranged so that its corresponding portion of the reference arm has a length such that the first portion of light can interfere with light that reflects off cornea C when first portion $B_{R1}$ and test beam $B_T$ are combined in detection beam $B_D$.

In some embodiments, the first mirror is fixed in a location to maintain a constant reference arm length. In such embodiments, apparatus 300 and the eye are moveable relative to one another, and an optical path length of the test arm (i.e., the length between the beam splitter and cornea C) is adjusted such that the optical path length of the test arm and the optical path length from the beam splitter to first mirror 340a are substantially equal. To achieve relative movement, the apparatus and/or the subject's eye may be movable. For example, movement of a subject's eye may be achieved using a subject positioning apparatus, such as movable chin rest (not shown). It will be appreciated that, when the test arm and the distance between the beam splitter and mirror 340a are substantially equal, interference will occur at a time during alteration of the reference arm optical path length by the variable delay optical element. Alteration of the reference arm by the variable delay optical element is described in greater detail below.

Second movable mirror 340b is disposed in the reference arm and adapted to intercept a second portion $B_{R2}$ of the reference beam $B_R$. Typically, the second mirror is movable (e.g., the mirror is motorized so as to be a scanning mirror) so that its corresponding portion of the reference arm can attain a length such that the second portion of light $B_{R2}$ can interfere with light that reflects from at least one second surface of the eye (e.g., a surface of the subject's lens and/or a surface of the retina) during alteration of the reference arm optical path length by the variable delay optical element. It will be appreciated that eye lengths typically vary among a population of subjects. Accordingly, the travel of second mirror 340b should be suitably selected.

Variable delay optical element 370 extends across the first portion of the reference beam and the second portion of the reference beam. Element 370 may be any suitable element that is made of at least partially transparent optical material. The element is configured such that element can be adjusted to alter the optical path lengths of the first portion of the reference arm and the second portion of the reference arm. For example, the element may vary its index of refraction or have an index of refraction greater than air and be variably oriented in arm portions $B_{R1}$ and $B_{R2}$ such that the beam portions travel a variable distance through the element. It will be appreciated that, only when element 370 is configured such that the first portion of the reference arm has an appropriate length will an interference signal corresponding to the cornea occur, and only when element 370 is configured such that the second portion of the arm has an appropriate length will an interference signal corresponding to the second surface of the eye occur.

In the illustrated embodiment, element 370 is a cube of transparent material (e.g., glass) configured to rotate about an axis X. However, the element may have any suitable configuration. For example, the element may be another optical delay element such as a prism translated across the optical paths such that the beams travel through varying distances of the glass as the prism is translated, or the optical delay element comprises a material that changes index of refraction in response to a voltage and as such need not be moved.

Although the delay apparatus described above are variable optical delay elements, in some embodiments, other variable delay apparatus can be used. For example, in some embodiments, first mirror and second mirror may be oscillated longitudinally to achieve a variable delay in the manner described above with reference to FIG. 2. For example, the mirrors may be located on a platform that is translated toward and away from beam splitter 220. While such apparatus may be appropriate for some embodiments, such apparatus are difficult to achieve constant speeds over large distances.

Detector 360 is adapted to receive light from the beam splitter. The light includes a combination of light reflected from eye E and light reflected from portions of reference arm $B_{R1}$, $B_{R2}$. The detector may include any suitable detector capable of receiving the light from the beam splitter and generating an electrical signal output that is indicative of the intensity of light incident on the detector. For example, the detector may be a photodiode.

Figure 4A:
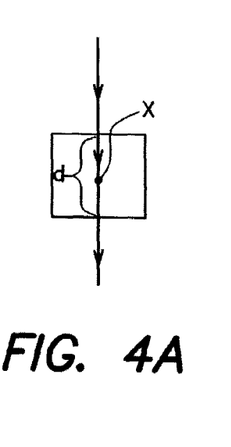
FIGS. 4A-4D illustrate an example of a delay element comprising a cube of glass adapted to rotate about an axis.
Figure 4B:
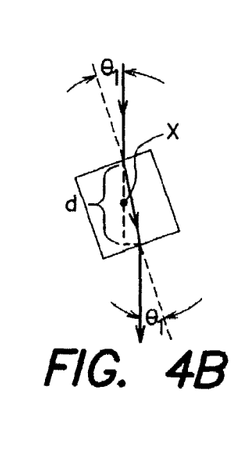
Figure 4C:
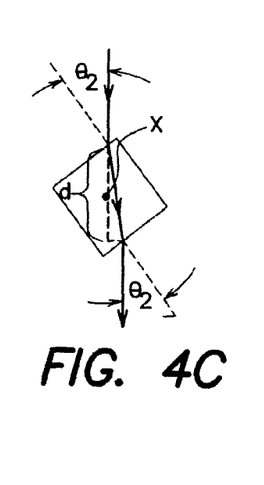
Figure 4D:
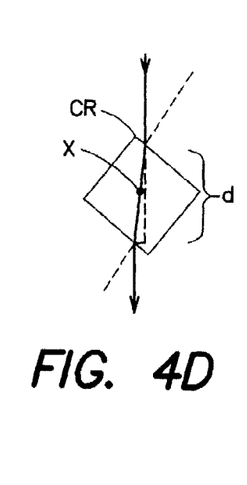

FIGS. 4A-4D illustrate further details of an example of a delay element as shown in FIG. 3 comprising a cube of glass adapted to rotate about an axis X. A representative beam of light is shown. As shown in FIG. 4A, in a first rotational position, the beam is incident normal to a first face and a second face of the cube and the beam travels a minimum distance d through the cube. In a second position (shown in FIG. 4B) the beam is projected through the first face and the second face at an angle $\theta_1$; accordingly the optical path length through the cube is a second distance, greater than first distance d. In a third position (shown in FIG. 4C) the beam is projected through the first face and the second face at angle $\theta_2$; accordingly the optical path length through the cube is a third distance, greater than first distance and second distance. FIG. 4D shows the beam after it has passed through corner CR.

Figure 5A:
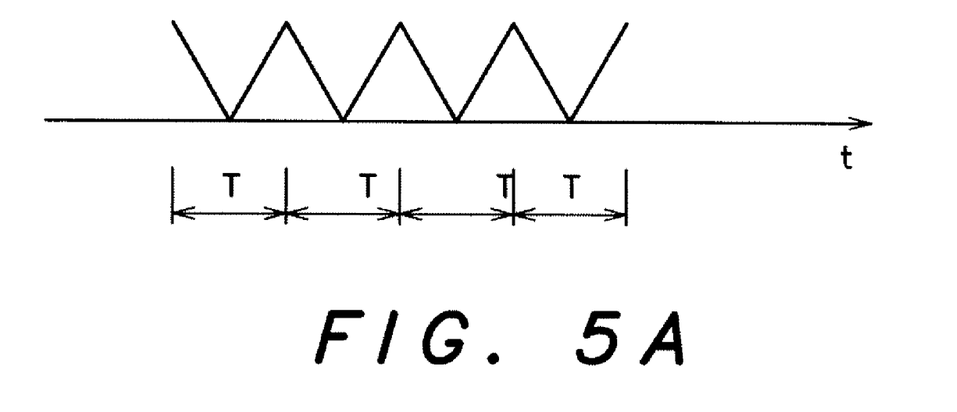
FIG. 5A illustrates the delay generated by the delay element of FIG. 4A as a function of time (also referred to herein as a delay signal)

FIG. 5A illustrates the delay as a function of time (referred to herein as a delay signal) provided by the cube as it rotates one complete rotation (i.e., the beam is rotated through each of the four faces of the cube). The beam is projected through each face over a period of time T. It will be appreciated that a delay signal is typically not embodied as an electronic signal; rather, it is a parameter of a variable delay apparatus.

It will be appreciated that, although only one beam is shown as being projected through the cube, multiple beams (e.g., the first portion of a reference beam and the second portion of the reference beam) may be projected the cube each having approximately a same delay. Although in the illustrated embodiment both portions of the reference beam are projected through a same delay element, separate delay elements may be used for each of the portion of reference beam.

Figure 5B:
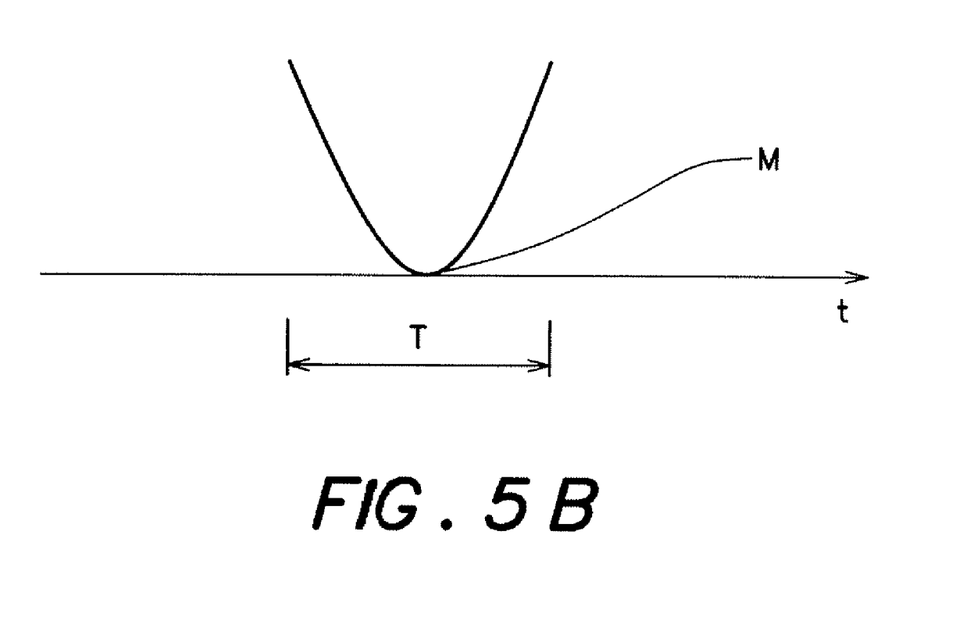
FIG. 5B illustrates an expanded view of the delay caused by projecting light through one face of the rotating delay element of FIG. 4A.

FIG. 5B illustrates an expanded view of the delay signal caused by one face of the cube. A minimum M is achieved when the beam is incident perpendicular to the face (shown in FIG. 3).

FIGS. 6A-6D illustrate outputs signals from the detector (as a function of time) taken as the optical path length is altered by delay element 370 (shown in FIG. 3). The time period in each of FIGS. 6A-6D is equal to two complete delay cycles of the delay element. A "delay cycle" is equal to the time needed for the delay element to cause an entire range of delays. For example, during a cycle the delay can vary from a maximum delay to a minimum delay, or from a minimum delay to a maximum delay (e.g., one-half of the signal shown in FIG. 5B).

Figure 6A:
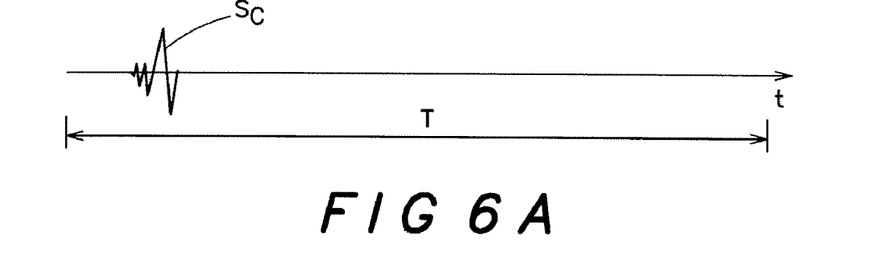
FIGS. 6A-6D illustrate outputs from a detector as a function of time, taken as the optical path length is altered by a delay element.
Figure 6B:
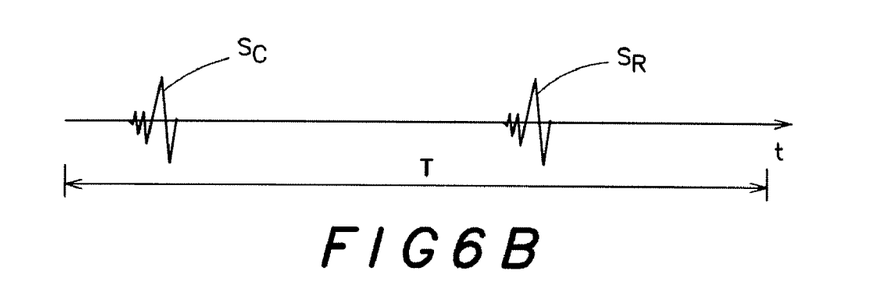

FIG. 6A illustrates an output of the detector when the relative position of the apparatus and the cornea is appropriate to generate a signal $S_C$ caused by interference of light from a first portion of the reference beam and light reflected from the cornea. It will be appreciated that, assuming that the length of the test arm is fixed, the location along the delay cycle at which the interference occurs is determined by the position of mirror 340a (shown in FIG. 3). FIG. 6B illustrates an output of the detector when the relative position of the apparatus and the cornea is appropriate to generate signal $S_C$, and the state of second mirror 340b (shown in FIG. 3) is appropriate to generate signal $S_R$ caused by interference of light from the second portion of reference beam with a beam reflected from a second surface of the eye other than the cornea (e.g., the retina).

It will be appreciated that a component of a signal influenced by interference may have multiple spikes. In some embodiments, a position of a corneal surface in signal $S_C$ is taken as the location of the peak of an envelope of the spikes in signal $S_C$. In some embodiments, a position of a retinal surface in signal $S_R$ is taken as the location of the peak of an envelope of the spikes in signal $S_R$. The peak of an envelope is referred to hereinbelow simply as an "interference peak." It will be appreciated that, although interference peaks are discussed in reference to a signal presented on a display, said peaks exist in space, independent of a display or sensor.

Figure 6C:
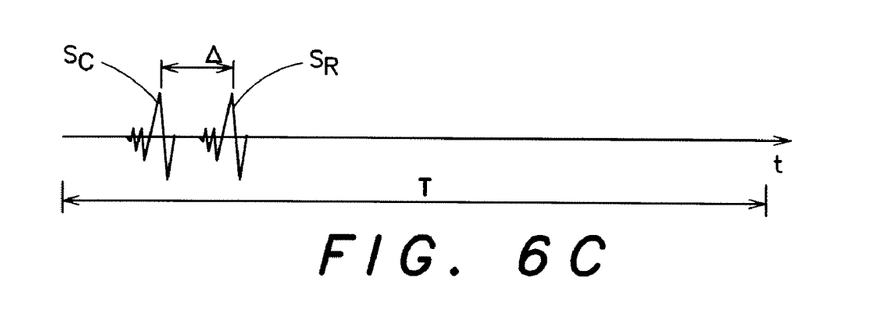

FIG. 6C illustrates that, by appropriately selecting the position of the second mirror, a non-zero time separation $\Delta$ between interference signal $S_C$ and the interference signal $S_R$ can be generated. The peak of signal $S_C$ is separated from peak $S_R$ by the distance $\Delta$. In some embodiments, the separation is selected such that the envelopes of signal $S_C$ is separated from the envelope of signal $S_R$ to facilitate measurement. In some embodiments, the envelopes are separated such that they do not overlap. The portion of the delay signal $\Delta$ between signal $S_R$ and signal $S_C$ is referred to herein as the measurement time interval of the delay signal (or simply the measurement time interval). Separation facilitates viewing of eye surface positions when displayed and facilitates accurate measurement.

In some embodiments, processor 380 (shown in FIG. 3) is adapted to control at least the second mirror such that such that a corneal interference peak and second interference peak have a predetermined non-zero separation.

According to aspects of the present invention, the first mirror and the second mirror are positioned (e.g., using processor 380) such that interference signal $S_C$ and interference signal $S_R$ occur at times such that the delay signal between signals $S_C$ and $S_R$ corresponds to a portion of the delay signal that is substantially linear.

The Applicant has determined that it is appropriate to select the positions of signal $S_R$ and signal $S_C$ such that the portion of the delay signal corresponding to the measurement time interval between said positions is substantially linear to increase the accuracy of measurements made by the apparatus.

It will be appreciated that the existence of a separation $\Delta$ means that, unlike conventional apparatus, the separation of the mirrors is not equal to an eye length. As set forth below, the separation may be accounted for to determine an eye length.

Figure 7:
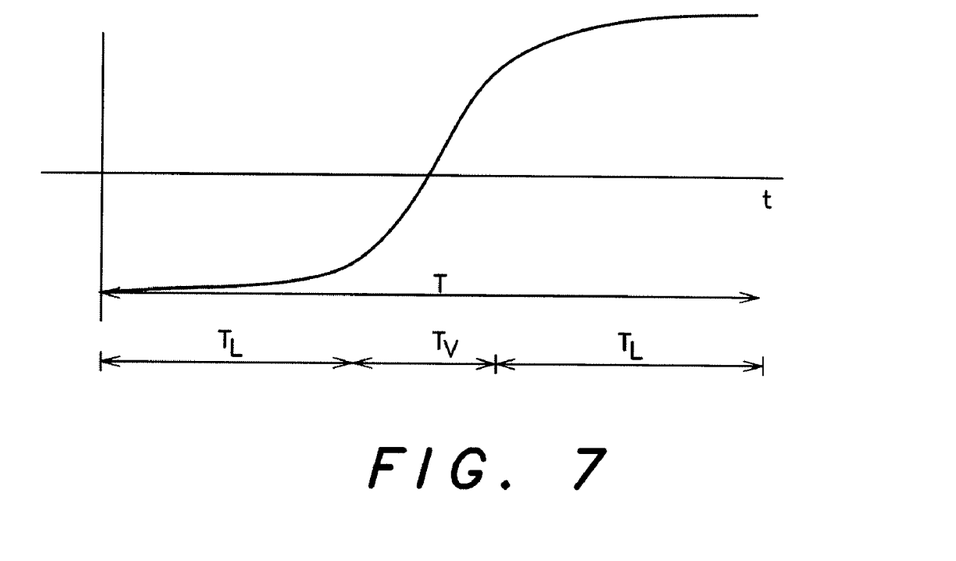
FIG. 7 is a graphical illustration of an approximation of a derivative of the delay as shown in FIG. 5B.

As defined herein, a degree of linearity of the delay signal is specified using a derivative of the delay signal. FIG. 7 illustrates a derivative of the delay shown in FIG. 5B. As shown in FIG. 7, a derivative of the delay as a function of time includes two regions $T_L$ having a substantially constant derivative and a region $T_{L'}$ where the derivative deviates significantly from constant.

According to aspects of the invention, first mirror 340a and second mirror 340b are positioned such that interference with a first surface of an eye (e.g., a corneal surface) and interference with a second surface of the eye (e.g., a retinal surface) occur such that the derivative of the delay changes less than 30% in the measurement time interval Δ. That is, the absolute value of the difference between the maximum derivative $D_{max}$ of the delay signal in measurement time interval and the minimum value of the derivative $D_{min}$ of the delay signal in the measurement time interval, divided by the minimum value of the derivative of the delay signal in the measurement time interval is less than 0.3.

$$0.0 \le \left| \frac{D_{max} - D_{min}}{D_{min}} \right| \le 0.3$$

In some embodiments, the absolute value of said calculated value is less than 10% and some embodiments it is less than 5%.

It will be appreciated that one face of a cube delay element (as shown in FIGS. 4A-4D) will provide two linear time intervals and a non-linear time interval. It will also be appreciated that other delay apparatus (e.g., other optical delay apparatus or mechanical apparatus will likewise have one or more linear time intervals), and a derivative of the delay provided by any such apparatus can be similarly calculated.

It will also be appreciated that, by selecting to make measurement in a substantially linear time interval, greater accuracy in length measurement can be achieved. In some embodiment, an output signal from detector 360 is filtered (e.g., using a bandpass filter) to increase the signal-to-noise of the output signal. In such embodiments, a benefit of using a substantially linear portion of the delay signal is that the frequency of the components of the signal generated by the interference signals (e.g., signals $S_C$ and $S_R$) will have a more uniform frequency thereby making filtering of the output signal more effective, and thereby increasing the signal-to-noise ratio. It will also be appreciated that, unlike some prior art apparatus, in apparatus according to aspects of the present invention mirrors 340a and 340b can be held stationary during measurement. Accordingly, it is not important that mirror 340b (shown in FIG. 3) be capable of highly linear movement.

Referring again to FIG. 3, in some embodiments, the apparatus is provided with a processor 380 programmed to control movement of mirror 340a and mirror 340b such that an appropriate measurement time interval can be achieved. According to aspects of the invention, the processor is adapted to control the second mirror to be positioned such that interference with a reflection from a first portion of the eye (e.g., a cornea) and the interference with the second portion of the eye (e.g., a retina) occur in a time interval of an output form detector 360 corresponding to a substantially linear delay signal. In some embodiments, mirror 340b is controlled such that the derivative of the delay signals changes less than 30% during the measurement time interval. In some embodiments, the derivative changes less than 10%, and some embodiments, the derivative of the delay changes less than 5%.

It will be appreciated that the apparatus can be configured so that a subject's cornea can be positioned relative to the apparatus such that interference signal $S_C$ occurs at a point in time where the change in delay is substantially linear (e.g. by relative positioning of the apparatus and the eye), and processor 380 controls only mirror 340b such that the measurement time interval occurs over a substantially linear time interval of the delay signal. However, in some embodiments, processor 380 controls both mirror 340a and 340b such that such that eye length measurement occurs over a substantially linear measurement time interval.

In some embodiments, it is advantageous if a display apparatus 390 is provided to display an output substantially as shown in FIGS. 6A-6C. In some such embodiments, delay cycles are completed fast enough that the display is in real time (i.e., at a rate of at least 1 measurement delay cycle per second, and preferably at a rate of at least 5 measurement delay cycles per second). It will be appreciated that a real time display provides an advantage that selection of a location on the cornea through which measurements are to be made (i.e., the location on the cornea through which a beam from source 310 is projected) can be more easily selected. For example, in patient's that have cataracts, by observing the presence and/or strength of the interference signals $S_C$ and $S_R$ while the test beam is projected on various portions of the subject's cornea, it can more easily be determined where measurements can be successfully made. In some embodiments in which multiple measurements are to be made and averaged together, 5 measurement delay cycles per second is appropriate, and in some embodiments 20 measurement delay cycles per second is appropriate. A suitable number of delay cycles per second can decrease the effects of patient movement during acquisition of multiple measurements.

Figure 6D:
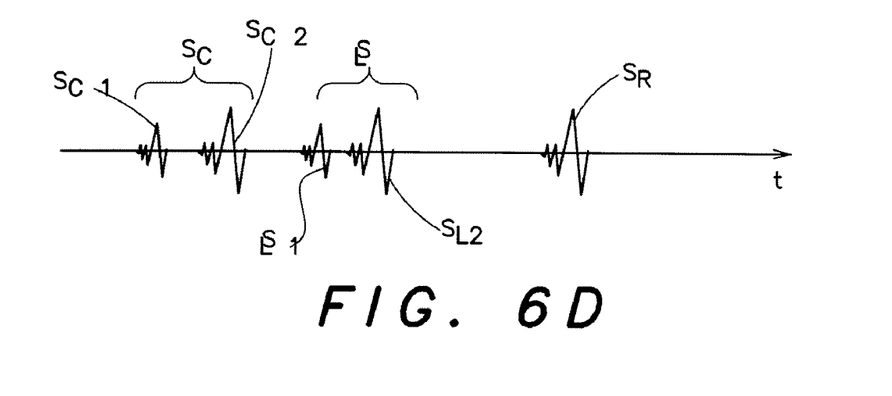

FIG. 6D illustrates that, in some embodiments, improved linearity of the output signals from the detector and improved sensitivity of signal detection are suitable such that signals $S_{C1}$, $S_{C2}$ corresponding to two surfaces of the cornea and signals $S_{L1}$, $S_{L2}$ corresponding to two surfaces of lens can be resolved. In such embodiments, distances between any suitable surfaces can be measured. For example, measurements of an eye's anterior chamber can be made taking advantage of the precision provided by aspects of the present invention. In some embodiments, the delay element provides a sufficient delay (i.e., change in the optical path length) of the reference arm such that signals $S_{C1}$, $S_{C2}$, $S_{L1}$, and $S_{L2}$ are all achieved using one portion of the reference beam (e.g., $B_{R1}$ in FIG. 3).

Figure 8:
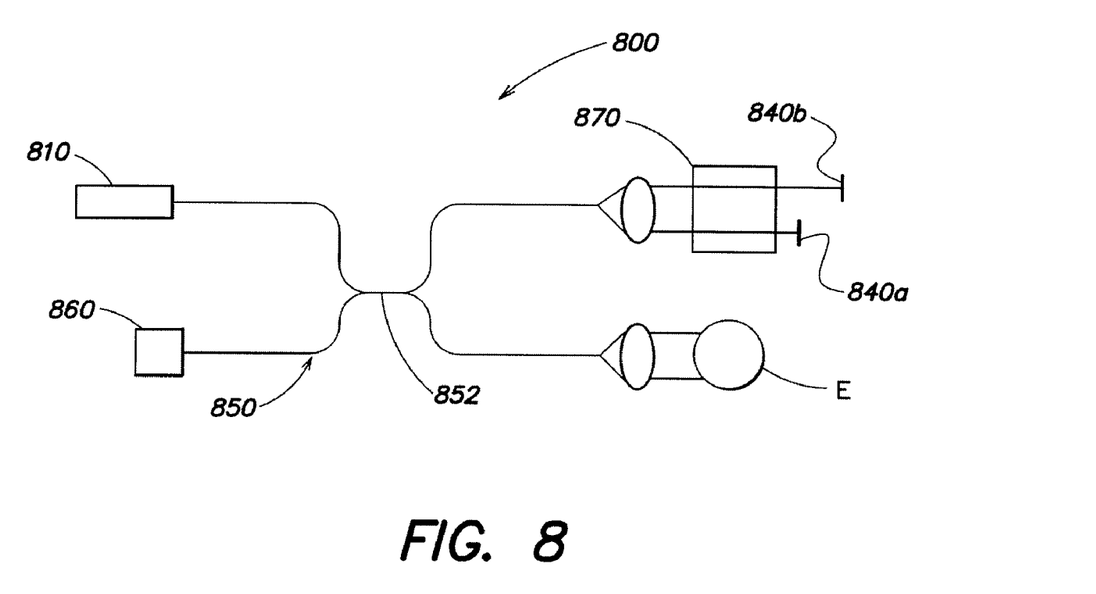
FIG. 8 illustrates another embodiment of an apparatus according to aspects of the present invention implemented using fiber optics.

FIG. 8 illustrates another embodiment of an axial eye length measurement apparatus 800 according to aspects of the present invention in which the interferometer is implemented using fiber optics 850. Axial eye length measurement apparatus comprises a light source 810 adapted to produce a beam of light, a beam splitter/combiner 852, a first mirror 840a, a second mirror 840b, a variable delay optical 870 element and a detector 860. Apparatus 800 includes a fiber optic that includes conventional fiber optic combining components and fiber optic splitting components. A processor (not shown) and display (not shown) as described above may be included.

An example of a configuration and procedure for using an apparatus according to aspects of the present invention is as follows. Reference is made to apparatus 300 in FIG. 3. In the present example procedure, it is assumed that a first mirror in the reference arm which reflects light to be interfered with light reflected from the cornea is fixed; and a second mirror in the reference arm that reflects light to be interfered with light reflected from the retina is movable (e.g., driven by a step motor). It is also assumed that the time interval(s) in a measurement cycle (as determined by the delay element) that correspond to a linear portion of the delay signal are known.

The subject's eye is positioned relative to apparatus 600 to achieve an interference signal between mirror 340a and the subject's cornea, the interference signal being located in a position corresponding to a linear portion of the delay signal. Initially, second mirror 340b is positioned such that the second mirror is 15 mm closer to beam splitter 320 than mirror 340a. It will be appreciated that 15 mm is considered shorter than the axial eye length of any normal human eye.

Mirror 340b is moved away from mirror 340a until the separation of the corneal peak and the retinal peak is approximately equal to an interval Δ. The value is selected as set forth above such that a linear portion of the delay signal is used in the measurement time interval. The mirror movements may be achieved by computer control or manually. A length (corresponding to an eye length minus a length corresponding to interval Δ) is thereby determined by the apparatus. It will be appreciated that interval Δ may be of a pre-selected length of time (e.g., where movement of mirror is under computer control); however, a pre-selected value is not necessary.

If multiple length values are to be averaged together to obtain a measured length, multiple lengths are determined and averaged together. As set forth above, by configuring apparatus 300 such that the delay measurement cycle is suitably short (e.g., by rotating a cube of glass suitably fast), measurements can be made with minimal patient movement.

After a final length value is obtained as determined by the separation of mirrors 340a and 340b (e.g., the value being either an average value or a single value), a distance corresponding to interval Δ (e.g., as determined by the index of refraction of the delay element and the rotation rate of the delay element), is added to the measured value to achieve a distance equal to the axial eye length. Accordingly, the separation Δ is compensated for and an eye length is attained. It will be appreciated that depending on the configuration of an apparatus and the positions of signals $S_C$ and $S_R$ in the output signal it may be appropriate to add or subtract a distance corresponding to interval Δ to achieve an appropriate length.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An axial eye length measurement apparatus for measuring
   an eye having a cornea and a second surface, comprising:
   a light source configured to produce a beam of partially coherent light;
   a beam splitter disposed in the beam and configured to project some of the light into a test arm and some of the light into a reference arm;
   a first mirror disposed in the reference arm to form a first reference path and configured to intercept a first portion of the light in the reference arm;
   a second movable mirror disposed in the reference arm to form a second reference path and configured to intercept a second portion of the light in the reference arm;
   a processor configured to control at least the second movable mirror such that a corneal interference peak formed using the first portion and the light in the test arm and a second interference peak formed using the second portion and the light in the test arm have a non-zero separation, wherein the processor is configured to control at least the second mirror such that the corneal peak and the second peak are separated from one another by a predetermined amount.

2. The apparatus of claim 1, wherein the processor is configured to control at least the second mirror such that an envelope corresponding to the corneal peak and an envelope of the second peak are separated from one another and do not overlap.

3. The apparatus of claim 1, further comprising at least one variable delay optical element extending across the first portion and the second portion, the delay element having a delay signal, wherein the delay signal corresponding to the region between the corneal interference peak and the second interference peak is substantially linear.

4. The apparatus of claim 3, wherein the derivative of the delay signal corresponding to the region between the corneal interference peak and the second interference peak changes by less than 30%.

5. The apparatus of claim 3, wherein the derivative of the delay signal corresponding to the region between the corneal interference peak and the second interference peak changes by less than 10%.

6. The apparatus of claim 3, wherein the derivative of the delay signal corresponding to the region between the corneal interference peak and the second interference peak changes by less than 5%.

7. The apparatus of claim 3, wherein the delay element generates delay cycles at a real time rate.

8. The apparatus of claim 1, further comprising a detector arranged to detect light in the corneal interference peak and light in the second interference peak, and generate an electric signal output.

9. The apparatus of claim 1, further comprising a display connected to the detector configured to display the corneal interference peak and the second interference peak.

10. The apparatus of claim 1, wherein the processor is configured to control the first mirror and the second mirror.

11. An axial eye length measurement apparatus, comprising:
    a light source configured to produce a beam of partially coherent light;
    a beam splitter disposed in the beam and configured to project light into a test arm and to project light into a reference arm;
    a first mirror disposed in the reference arm and configured to intercept a first portion of the light in the reference arm;
    a second movable mirror disposed in the reference arm and configured to intercept a second portion of the light in the reference arm; and
    a variable delay optical element extending across the first portion and the second portion.

12. A method of measuring an eye length, comprising:
    projecting partially coherent light
    directing a first portion of the light onto an eye having a cornea;
    directing a second portion of the light into a reference arm, a first part of the second portion of the light incident on a first mirror, and a second part of the second portion of the light incident on a second mirror;
    variably delaying the first part;
    variably delaying the second part;
    interfering the first part with the first portion to form a corneal interference peak; and
    interfering the second part with the first portion to form a second interference peak; and
    positioning the second mirror and the first mirror relative to one another such that the corneal interference peak and the second interference peak have a non-zero separation wherein the separation is predetermined.

13. The method of claim 12, wherein the steps of variably delaying the first part and variably delaying the second part are achieved using a same variable delay element.

14. The method of claim 12, wherein the non-zero separation corresponds to a linear portion of a delay signal of an apparatus causing the variable delay.

15. The method of claim 14, wherein the non-zero separation corresponds to a portion of the delay signal having a derivative that changes by less than 30% between the corneal interference peak and the second interference peak.

16. The method of claim 15, wherein the non-zero separation corresponds to a portion of the delay signal having a derivative that changes by less than 10% between the corneal interference peak and the second interference peak.

17. The method of claim 14, wherein the non-zero separation corresponds to a portion of the delay signal having a derivative that changes by less than 5% between the corneal interference peak and the second interference peak.

18. The method of claim 12, further comprising displaying the corneal interference peak and the second interference peak.

19. The method of claim 12, further comprising displaying the corneal interference peak and the second interference peak at a real time rate.

* * * * *